United States Patent
Humphrey et al.

(10) Patent No.: US 6,750,220 B2
(45) Date of Patent: Jun. 15, 2004

(54) AMINE SALT OF AN INTEGRIN RECEPTOR ANTAGONIST

(75) Inventors: Guy R. Humphrey, Hillsborough, NJ (US); Wei Xu, North Wales, PA (US)

(73) Assignee: Merck & Co., Inc., Rahway, NJ (US)

(*) Notice: Subject to any disclaimer, the term of this patent is extended or adjusted under 35 U.S.C. 154(b) by 30 days.

(21) Appl. No.: 10/174,016

(22) Filed: Jun. 18, 2002

(65) Prior Publication Data

US 2003/0004171 A1 Jan. 2, 2003

Related U.S. Application Data

(60) Provisional application No. 60/299,344, filed on Jun. 19, 2001.

(51) Int. Cl.⁷ ..................... C07D 401/14; A61K 31/14
(52) U.S. Cl. ........................... 514/256; 544/333
(58) Field of Search ............... 514/256; 544/333

(56) References Cited

U.S. PATENT DOCUMENTS 6,048,861 A     4/2000  Askew et al. .............. 544/333
6,444,680 B1 *  9/2002  Humphrey et al. ......... 514/256

FOREIGN PATENT DOCUMENTS

WO      WO 99/31061    6/1999

OTHER PUBLICATIONS

Gu, L., et al., Pharmaceutical Research, (1987) pp. 255–257, vol. 4, No. 3.
Stahl, P. H., Wermuth, C. G.,(2002) pp. 324–325, Wiley–VCH.

* cited by examiner

Primary Examiner—Richard L. Raymond
Assistant Examiner—Tamthom N. Truong
(74) Attorney, Agent, or Firm—Patricia A. Shatynski; Mark R. Daniel

(57) ABSTRACT

The tris(hydroxymethyl)aminomethane ("TRIS") salt of 3-(pyrimidin-5-yl)-9-(5,6,7,8-tetrahydro-[1,8]-naphthyridin-2-yl)-nonanoic acid is a potent antagonist of the integrin αvβ3 receptor and is useful for the prevention and/or treatment of osteoporosis and vascular restenosis, as well as conditions associated with excessive angiogenesis, such as macular degeneration, diabetic retinopathy, atherosclerosis, inflammatory arthritis, cancer, and metastatic tumor growth. The invention also relates to a process for the preparation of the novel salt as well as pharmaceutical compositions containing the salt and methods of using the salt.

16 Claims, 4 Drawing Sheets

AMINE SALT OF AN INTEGRIN RECEPTOR ANTAGONIST

CROSS-REFERENCE TO RELATED APPLICATIONS

The present invention is related to U.S. provisional application Serial No. 60/299,344, filed Jun. 19, 2001, the contents of which are hereby incorporated by reference.

FIELD OF THE INVENTION

The present invention relates to a novel amine salt of an integrin receptor antagonist. More particularly, the invention relates to the tris(hydroxymethyl)aminomethyl ("TRIS") salt of 3-(pyrimidin-5-yl)-9-(5,6,7,8-tetrahydro-[1,8]-naphthyridin-2-yl)-nonanoic acid, which is a potent integrin $\alpha_v\beta_3$ receptor antagonist. The "TRIS" salt of the present invention is therefore useful for the treatment and prevention of diseases and conditions for which an antagonist of the integrin $\alpha_v\beta_3$ receptor is indicated.

BACKGROUND OF THE INVENTION

Integrin $\alpha_v\beta_3$ receptor antagonists have been described as being of use for the prevention and/or treatment of osteoporosis, vascular restenosis, macular degeneration, diabetic retinopathy, atherosclerosis, inflammatory arthritis, cancer, and metastatic tumor growth [see, for example, M. E. Duggan, et al., "Ligands to the integrin receptor $\alpha_v\beta_3$, $Exp.$ $Opin.$ $Ther.$ $Patents$, 10: 1367–1383 (2000); M. Gowen, et al., "Emerging therapies for osteoporosis," $Emerging$ $Drugs$, 5: 1–43 (2000); J. S. Kerr, et al., "Small molecule $\alpha_v$ integrin antagonists: novel anticancer agents," $Exp.$ $Opin.$ $Invest.$ $Drugs$, 9: 1271–1291 (2000); and W. H. Miller, et al., "Identification and in vivo efficacy of small-molecule antagonists of integrin $\alpha_v\beta_3$ (the vitronectin receptor)," $Drug$ $Discovery$ $Today$, 5: 397–408 (2000)].

U.S. Pat. No. 6,048,861, assigned to Merck & Co., describes a class of 9-substituted-3-aryl-nonanoic acid derivatives, which are potent integrin $\alpha_v\beta_3$ receptor antagonists and therefore useful for inhibiting bone resorption, vascular restenosis, treating and/or preventing osteoporosis, and inhibiting diseases and conditions associated with excessive and undesirable angiogenesis. Specifically disclosed in U.S. Pat. No. 6,048,861 is 3-(pyrimidin-5-yl)-9-(5,6,7,8-tetrahydro-[1,8]-naphthyridin-2-yl)-nonanoic acid, including the enantiomeric 3(R) and 3(S) forms. Pharmaceutically acceptable salts of this compound are generically encompassed within the scope of U.S. Pat. No. 6,048,861.

However, there is no specific disclosure in the above reference of the newly discovered tris(hydroxymethyl) aminomethyl ("TRIS") salt of 3-(pyrimidin-5-yl)-9-(5,6,7,8-tetrahydro-[1,8]-naphthyridin-2-yl)-nonanoic acid of structural formula I below.

SUMMARY OF THE INVENTION

This invention provides the novel tris(hydroxymethyl) aminomethyl ("TRIS") salt of 3-(pyrimidin-5-yl)-9-(5,6,7,8-tetrahydro-[1,8]-naphthyridin-2-yl)-nonanoic acid of the following structural formula I:

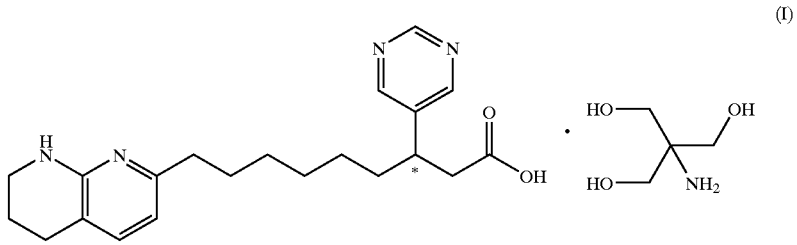

(I)

or a pharmaceutically acceptable solvate, including hydrate, thereof.

The "TRIS" salt of the present invention has a chiral center (indicated with an *) at the C-3 position of the nonanoic acid chain and can thus occur as a racemate, racemic mixture, and single enantiomers, with all isomeric forms being included in the present invention. The separate enantiomers, substantially free of the other, are included within the scope of the invention, as well as mixtures of the two enantiomers.

Therefore, one embodiment of the present invention provides the TRIS salt of 3(S)-(pyrimidin-5-yl)-9-(5,6,7,8-tetrahydro-[1,8]-naphthyridin-2-yl)-nonanoic acid of structural formula II:

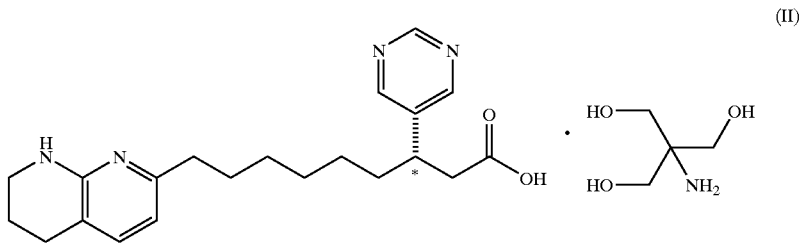

(II)

A second embodiment of the present invention provides the "TRIS" salt of 3(R)-(pyrimidin-5-yl)-9-(5,6,7,8-tetrahydro-[1,8]-naphthyridin-2-yl)-nonanoic acid of structural formula III:

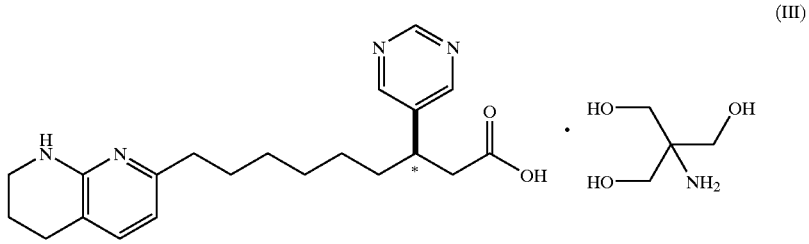

More specifically, the "TRIS" salt of the present invention is comprised of one molar equivalent of 3-(pyrimidin-5-yl)-9-(5,6,7,8-tetrahydro-[1,8]-naphthyridin-2-yl)-nonanoic acid anion and one molar equivalent of protonated tris (hydroxymethyl)aminomethane cation.

In a further embodiment of the present invention, the "TRIS" salts of structural formulae I–III are crystalline.

The crystalline "TRIS" salt of structural formula I exhibits improved chemical and physical properties over the parent zwitterionic compound of structural formula IV below. This salt therefore has advantages for the preparation of solid pharmaceutical dosage forms containing the pharmacologically active ingredient. Moreover, the "TRIS" salt has greater solubility in water than the parent zwitterionic compound rendering it more desirable for the preparation of aqueous formulations containing the active ingredient suitable for parenteral, such as intravenous, administration.

The "TRIS" salt of the present invention, which exhibits potent integrin $\alpha_v\beta_3$ antagonist activity, is particularly useful for inhibiting bone resorption, treating and/or preventing osteoporosis, and inhibiting vascular restenosis, diabetic retinopathy, macular degeneration, atherosclerosis, inflammatory arthritis, cancer, and metastatic tumor growth.

DETAILED DESCRIPTION OF THE INVENTION

Figure 1:
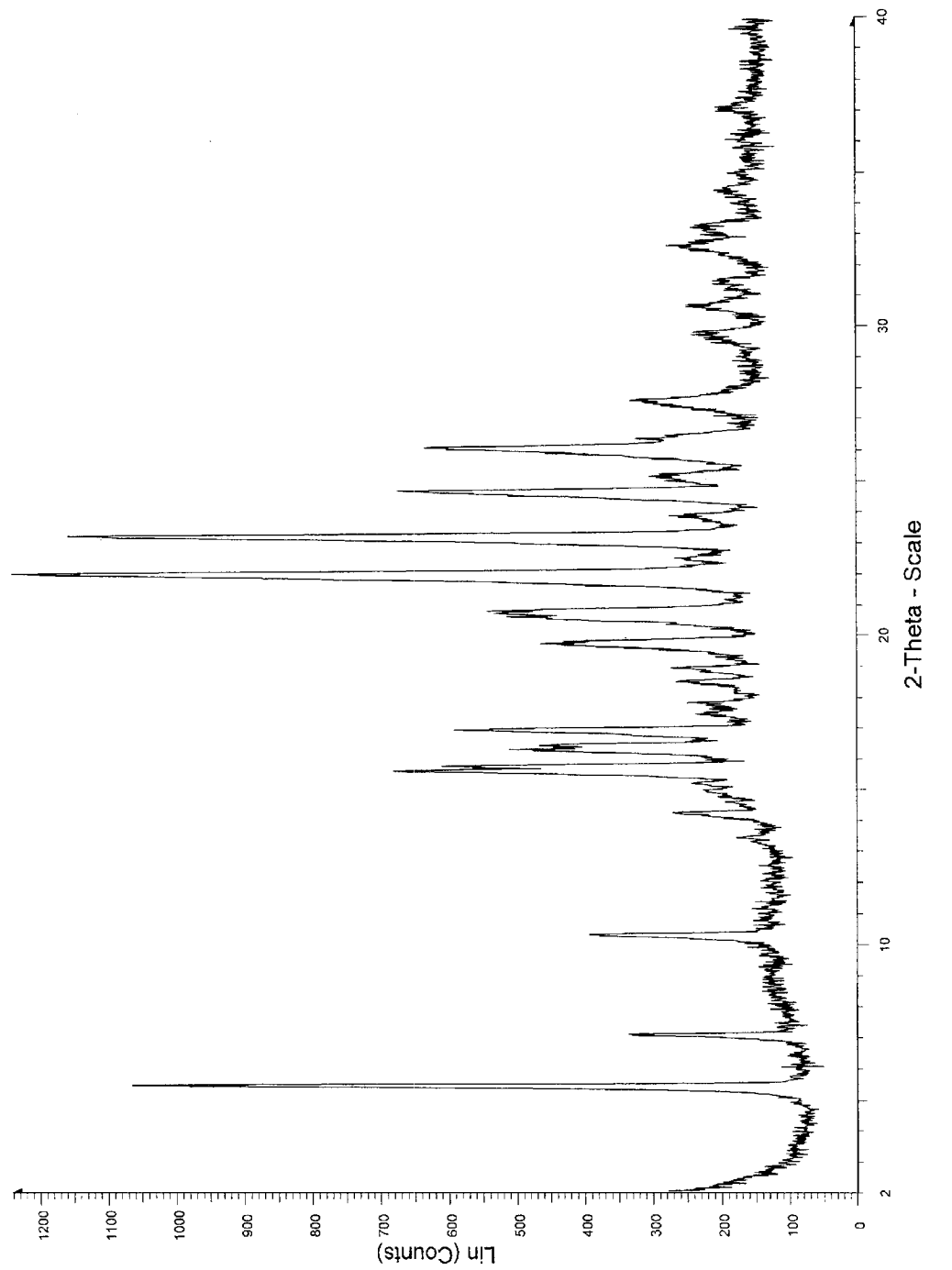
FIG. 1 is a characteristic X-ray diffraction pattern of the crystalline tris(hydroxymethyl)aminomethane salt of structural formula I.

The present invention provides a pharmaceutical composition comprising the tris(hydroxymethyl)aminomethane salt of structural formula I above, or a pharmaceutically acceptable solvate thereof, in association with one or more pharmaceutically acceptable carriers.

The compositions in accordance with the invention are suitably in unit dosage forms such as tablets, pills, capsules, powders, granules, sterile solutions or suspensions, metered aerosol or liquid sprays, drops, ampoules, auto-injector devices or suppositories. The compositions are intended for oral, parenteral, intranasal, sublingual, or rectal administration, or for administration by inhalation or insufflation. Formulation of the compositions according to the invention can conveniently be effected by methods known from the art, for example, as described in *Remington's Pharmaceutical Sciences*, 17$^{th}$ ed., 1995.

The dosage regimen is selected in accordance with a variety of factors including type, species, age, weight, sex and medical condition of the patient; the severity of the condition to be treated; the route of administration; and the renal and hepatic function of the patient. An ordinarily skilled physician, veterinarian, or clinician can readily determine and prescribe the effective amount of the drug required to prevent, counter, or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, the salt of the present invention may be administered in a single daily dose, or the total daily dosage may be administered in divided doses of two, three or four times daily. Furthermore, the salt of the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In the methods of the present invention, the salt herein described in detail can form the active ingredient, and is typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug component can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

According to a further aspect, the present invention provides a process for the preparation of the tris (hydroxymethyl)aminomethyl ("TRIS") salt of formula I, which process comprises reacting 3-(pyrimidin-5-yl)-9-(5,6,7,8-tetrahydro-[1,8]-naphthyridin-2-yl)-nonanoic acid of structural formula IV below:

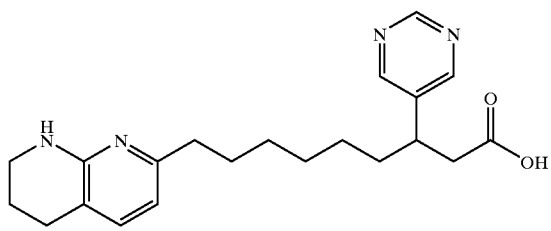

(IV)

with approximately one molar equivalent of tris (hydroxymethyl)aminomethane in a suitable organic solvent. The process is carried out generally at about 0° C. to about 100° C., and preferably at about 20° to about 60° C. Generally, the organic solvent is a linear or branched $C_1$–$C_4$ alcohol, such as methanol, ethanol, or isopropanol, or a mixture thereof. In one embodiment, the solvent used for the salt formation is a mixture of methanol and ethanol. Salt crystallization is then effected by adding a replacement solvent, such as ethyl acetate or isopropyl acetate, and removing the lower boiling alcohol mixture by distillation while maintaining the volume of the replacement solvent constant. In one embodiment the replacement solvent is isopropyl acetate. Crystallization of the salt can be accelerated by seeding the alcohol solution with crystals of the authentic "TRIS" salt prior to solvent replacement with ethyl or isopropyl acetate. The "TRIS" salt is then isolated and purified by conventional procedures, such as by filtration and drying.

The starting compound of structural formula IV was prepared by the procedures described in U.S. Pat. No. 6,048,861, which is incorporated by reference herein in its entirety.

In a still further aspect, the present invention provides a method for the treatment and/or prevention of clinical conditions for which an integrin αvβ3 receptor antagonist is indicated, which method comprises administering to a patient in need of such prevention or treatment a prophylactically or therapeutically effective amount of the salt of structural formula I as defined above or a pharmaceutically acceptable solvate thereof.

The present invention also provides the use of the salt of structural formula I as defined above or pharmaceutically acceptable solvate thereof for the manufacture of a medicament for the prevention and/or treatment of clinical conditions for which an antagonist of the integrin αvβ3 receptor is indicated.

The following non-limiting Examples are intended to illustrate the present invention and should not be construed as being limitations on the scope or spirit of the instant invention.

All X-ray patterns were obtained on a Siemens D5000 X-ray diffractometer, using Cu Kα radiation. All DSC thermograms were taken on a TA 2920 Differential Scanning Calorimeter with a heating rate of 10° C./minute under nitrogen. The carbon-13 CPMAS nuclear magnetic resonance (NMR) spectra were collected with a 200 MHz Varian Inova solid-state NMR spectrometer; a contact time of 1.5 seconds and a pulse delay of 5 seconds were used for all samples. The FT-infrared spectra were obtained using a Perkin Elmer FT-IR Spectrum One spectrometer; spectra were collected at 4 $cm^{-1}$ resolution. The thermogravimetric analysis (TGA) was performed on a Perkin-Elmer 7 Thermal Analysis series at a heating rate of 10° C./min.

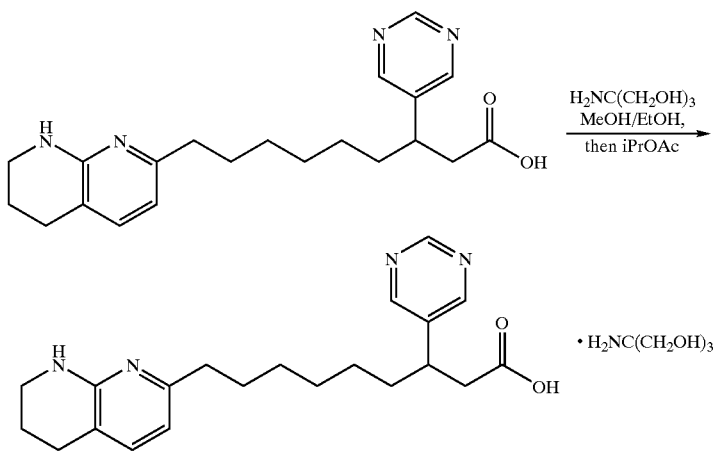

EXAMPLE 1

3(R or S)-(Pyrimidin-5-yl)-9-(5,6,7,8-tetrahydro-[1,8]naphthyridin-2-yl)-nonanoic acid tris (hydroxymethyl)aminomethane salt 3(R or S)-(Pyrimidin-5-yl)-9-(5,6,7,8-tetrahydro-[1,8] naphthyridin-2-yl)-nonanoic acid (prepared as described in U.S. Pat. No. 6,048,861, which is incorporated herein by reference in its entirety) (7.12 g, 19.2 mmol) was dissolved in warm (about 40° C.) ethanol (about 70 mL) and filtered to remove insolubles. Tris(hydroxymethyl)aminomethane (2.367 g, 19.5 mmol) was dissolved in warm (about 60° C.) methanol (about 35 mL) which was filtered directly into the above ethanolic solution of the zwitterionic compound. The mixture was seeded with crystals of the authentic "tris" salt and concentrated. The slurry was aged for 2–3 hours and then concentrated under diminished pressure at constant volume by adding isopropyl acetate (total of about 200 mL). The resultant slurry was cooled to 20° C., aged for one hour, and filtered. The solid was washed with isopropyl acetate and dried in vacuo at 20° C.

The X-ray powder diffraction pattern of the crystalline tris(hydroxymethyl)aminomethane ("TRIS") salt is illustrated in FIG. 1. It has characteristic diffraction peaks corresponding to d-spacings of 16.38, 12.55, 8.62, 6.23, 5.69, 5.64, 5.44, 5.40, 5.24, 4.50, 4.31, 4.28, 4.05, 3.83, 3.61, 3.42, and 3.23 angstroms.

Figure 2:
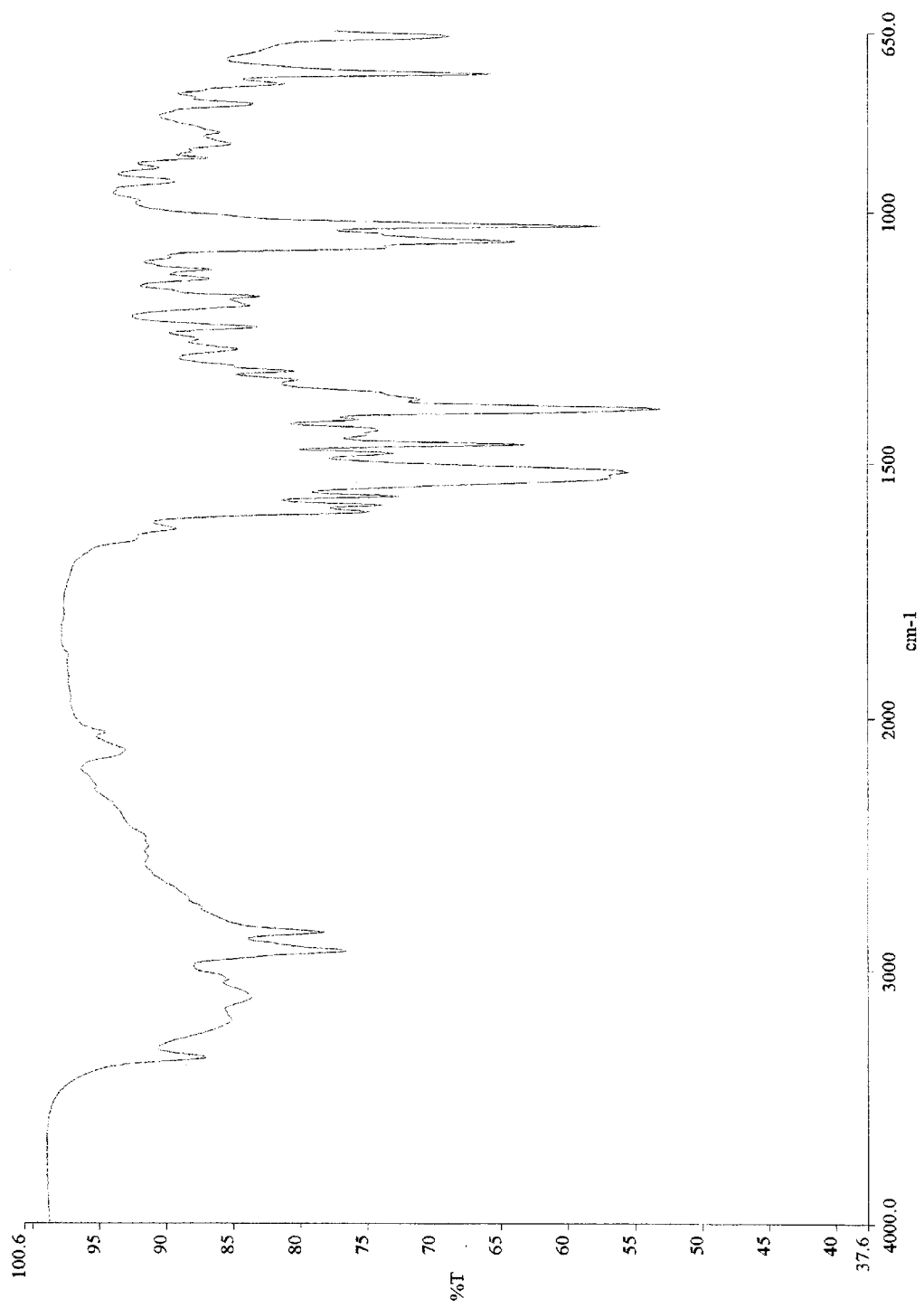
FIG. 2 is an FT infrared spectrum (FT-IR) of the crystalline tris(hydroxymethyl)aminomethane salt of structural formula I.

The FT infrared spectrum of the crystalline anhydrous "TRIS" salt is illustrated in FIG. 2, which exhibits significant absorption bands at 3347, 3199, 3110, 3040, 2929, 2853, 1599, 1586, 1567, 1529, 1519, 1464, 1390, 1232, 1188, 1171, 1063, 1031, 733, and 659 $cm^{-1}$.

Figure 3:
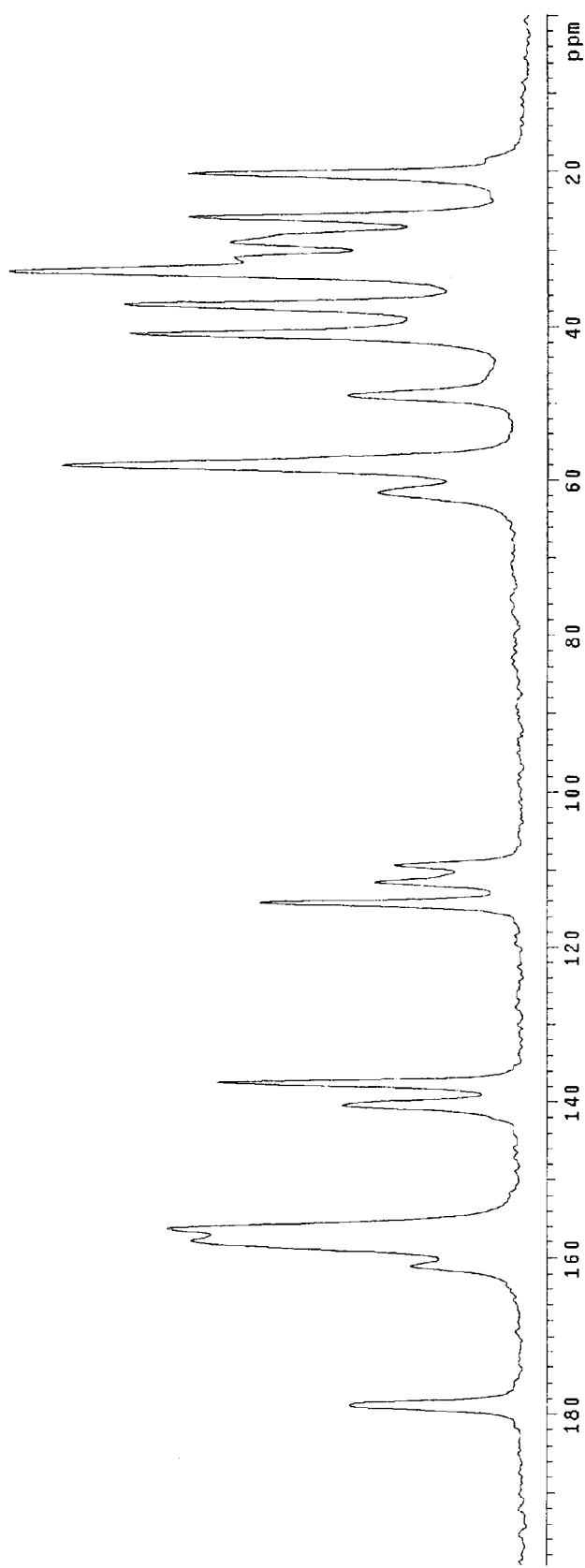
FIG. 3 is a carbon-13 cross-polarization magic-angle spinning (CPMAS) nuclear magnetic resonance (NMR) spectrum of the crystalline tris(hydroxymethyl)aminomethane salt of structural formula I.

The crystalline "TRIS" salt was also characterized by solid-state NMR spectroscopy. FIG. 3 illustrates the carbon-13 CPMAS NMR spectrum of the crystalline salt which exhibits signals with chemical shift values at 179.0, 161.1, 158.2, 156.6, 140.6, 137.7, 114.4, 111.6, 109.5, 61.7, 58.3, 49.0, 41.1, 37.3, 33.2, 29.2, 26.0, and 20.4 ppm.

Figure 4:
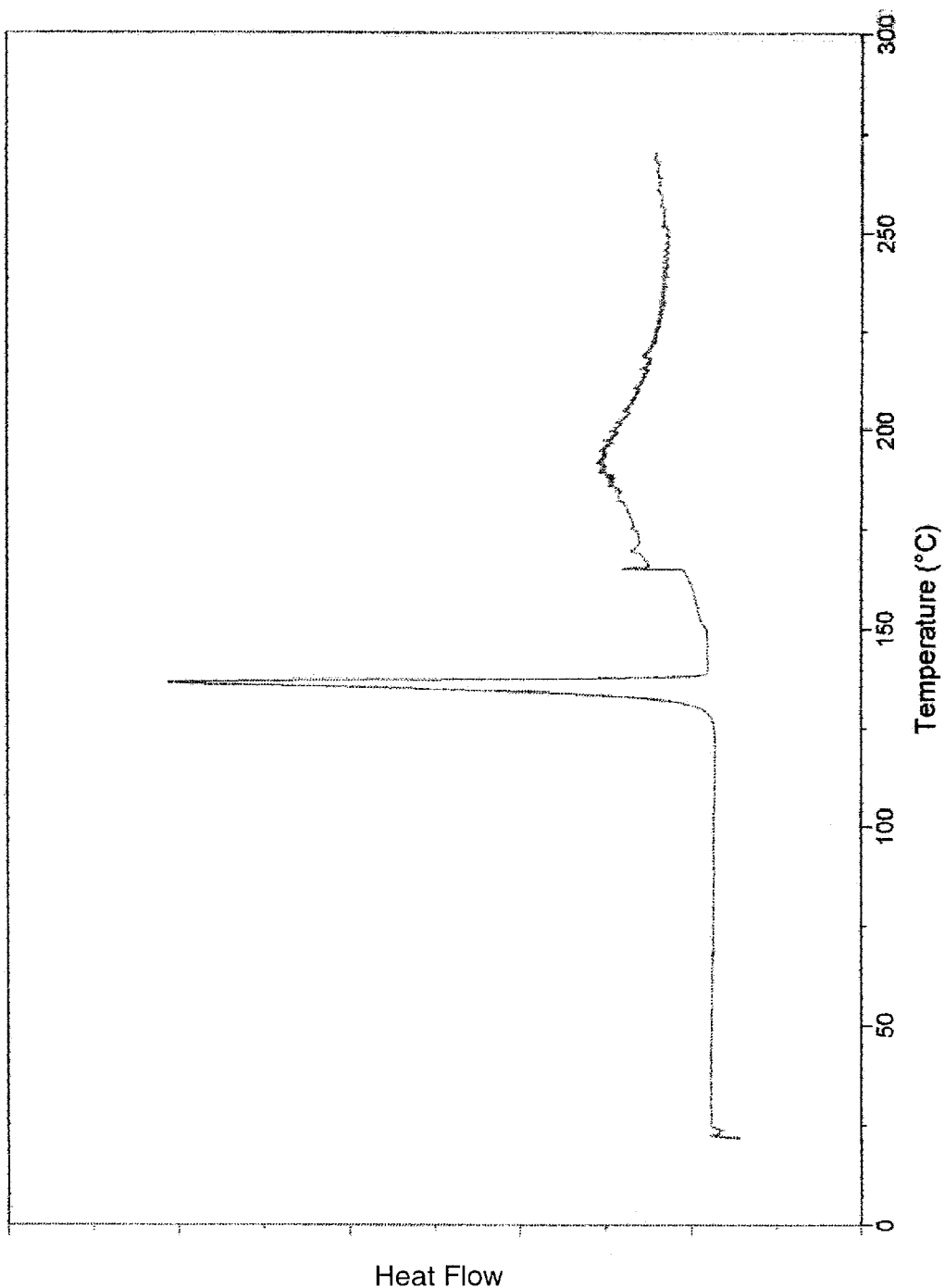
FIG. 4 is a differential scanning calorimetric (DSC) curve of the crystalline tris(hydroxymethyl)aminomethane salt of structural formula I.

The differential scanning calorimeter (DSC) curve of the crystalline anhydrous "TRIS" salt is illustrated in FIG. 4. The DSC curve exhibits a melting/decomposition endotherm with a peak temperature of about 137° C. (extrapolated onset temperature of about 134° C.).

The content of water as obtained with Karl-Fischer titration was about 0.6 wt %. Thermogravimetric analysis (TGA) indicated a weight loss of about 0.5% from ambient temperature to about 160° C.

EXAMPLE 2

3(S or R)-(Pyrimidin-5-yl)-9-(5,6,7,8-tetrahydro-[1,8]naphthyridin-2-yl)-nonanoic acid tris(hydroxymethyl)aminomethane salt The enantiomeric "TRIS" salt was prepared from 3(S or R)-(pyrimidin-5-yl)-9-(5,6,7,8-tetrahydro-[1,8]naphthyridin-2-yl)-nonanoic acid as described in Example 1.

EXAMPLES OF PHARMACEUTICAL FORMULATIONS

The tris(hydroxymethyl)aminomethane salt of formula I can be formulated into a tablet by a direct compression process. A 100 mg potency tablet is composed of 133 mg of the active ingredient, 243 mg lactose, 20 mg of croscarmellose sodium, and 4 mg of magnesium stearate. The active ingredient, lactose, and croscarmellose sodium are first blended, and the mixture is then lubricated with magnesium stearate and pressed into tablets.

An intravenous (i.v.) aqueous formulation is prepared by dissolving the "TRIS" amine salt of structural formula I in normal saline. For a formulation with a concentration of 5 mg/mL, 6.65 mg of the active ingredient is dissolved in one mL normal saline.

What is claimed is:

1. An amine salt of 3-(pyrimidin-5-yl)-9-(5,6,7,8-tetrahydro-[1,8]-naphthyridin-2-yl)-nonanoic acid of structural formula I:

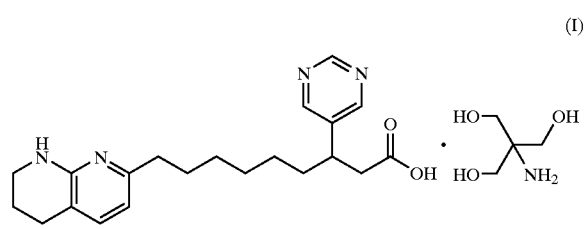

(I)

or a pharmaceutically acceptable solvate, including hydrate, thereof.

2. The salt of claim 1 of structural formula II having the (S)-configuration at the chiral center marked with an *

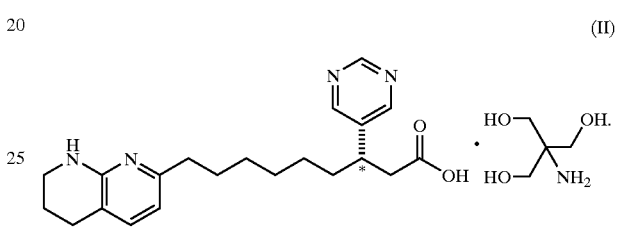

(II)

3. The salt of claim 1 of structural formula m having the (R)-configuration at the chiral center marked with an *

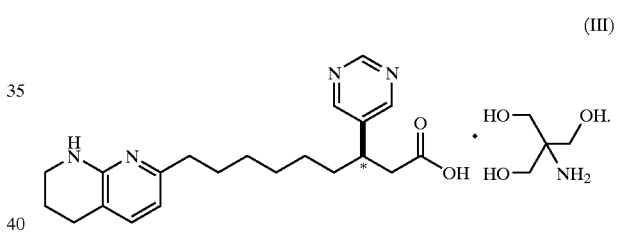

(III)

4. The crystalline salt of claim 1 characterized by an X-ray powder diffraction pattern showing diffraction peaks corresponding to d-spacings of 16.38, 12.55, 8.62, 6.23, 5.69, 5.64, 5.44, 5.40, 5.24, 4.50, 4.31, 4.28, 4.05, 3.83, 3.61, 3.42, and 3.23 angstroms.

5. The crystalline salt of claim 1 characterized by a solid-state carbon-13 CPMAS nuclear magnetic resonance spectrum showing signals at 179.0, 161.1, 158.2, 156.6, 140.6, 137.7, 114.4, 111.6, 109.5, 61.7, 58.3, 49.0, 41.1, 37.3, 33.2, 29.2, 26.0, and 20.4 ppm.

6. The crystalline salt of claim 4 characterized by an FT-infrared spectrum showing significant absorption bands at 3347, 3199, 3110, 3040, 2929, 2853, 1599, 1586, 1567, 1529, 1519, 1464, 1390, 1232, 1188, 1171, 1063, 1031, 733, and 659 $cm^{-1}$.

7. A salt comprising the ions of 3-(pyrimidin-5-yl)-9-(5,6,7,8-tetrahydro-[1,8]-naphthyridin-2-yl)-nonanoic acid anion and protonated tris(hydroxymethyl)aminomethane cation.

8. A pharmaceutical composition comprising a prophylactically or therapeutically effective amount of the salt according to claim 1 or a pharmaceutically acceptable solvate thereof in association with one or more pharmaceutically acceptable carriers.

9. A method for the prevention and/or treatment of osteoporosis comprising administering to a patient in need of such prevention or treatment a prophylactically or therapeutically effective amount of the salt according to claim 1, or a pharmaceutically acceptable solvate thereof.

10. A method for the treatment of a disease or condition characterized by excessive angiogenesis comprising administering to a patient in need of such treatment a therapeutically effective amount of the salt according to claim 1, or a pharmaceutically acceptable solvate thereof.

11. A method for the treatment of a disease or condition comprising administering to a patient in need of such treatment, a therapeutically effective amount of the salt according to claim 1, or a pharmaceutically acceptable solvate thereof, wherein said disease or condition is selected from the group consisting of macular degeneration, vascular restenosis, diabetic retinopathy, atherosclerosis, inflammatory arthritis, cancer, and metastatic tumor growth.

12. A process for preparing the amine salt of claim 1 comprising the step of contacting one molar equivalent of 3-(pyrimidin-5-yl)-9-(5,6,7,8-tetrahydro-[1,8]-naphthyridin-2-yl)-nonanoic acid in an organic solvent with about a one molar equivalent of tris(hydroxymethyl)aminomethane at a temperature in the range of about 0° C. to about 100° C.

13. The process of claim 12 wherein said organic solvent is methanol, ethanol, isopropanol, or a mixture thereof.

14. The pharmaceutical composition of claim 8 adapted for i.v. administration.

15. The tris(hydroxymethyl)aminomethane salt of 3-(pyrimidin-5-yl)-9-(5,6,7,8-tetrahydro-[1,8]-naphthyridin-2-yl)-nonanoic acid prepared according to the process of claim 12

16. The crystalline salt of claim 4 characterized in being anhydrous.

* * * * *